United States Patent
Matsumoto

(10) Patent No.: US 8,716,641 B2
(45) Date of Patent: May 6, 2014

(54) SCANNING IMAGING DEVICE FOR IMAGING TARGET ON A SUBSTRATE

(75) Inventor: Kazuhiro Matsumoto, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 325 days.

(21) Appl. No.: 12/744,575

(22) PCT Filed: Apr. 2, 2009

(86) PCT No.: PCT/JP2009/057234
§ 371 (c)(1),
(2), (4) Date: May 25, 2010

(87) PCT Pub. No.: WO2009/123359
PCT Pub. Date: Oct. 8, 2009

(65) Prior Publication Data
US 2010/0230580 A1    Sep. 16, 2010

(30) Foreign Application Priority Data
Apr. 2, 2008   (JP) ................. 2008-096145

(51) Int. Cl.
*G02B 7/04* (2006.01)
*G06M 7/00* (2006.01)
*H01J 3/14* (2006.01)

(52) U.S. Cl.
USPC ......... 250/201.4; 250/235; 250/221; 250/216

(58) Field of Classification Search
USPC .......... 359/196.1, 197.1, 201.1, 201.2, 202.1, 359/204.1, 212.1, 213.1, 214.1, 215.1, 359/216.1, 219.2, 383; 250/208.1, 347, 250/348, 201.2–201.8, 559.04, 559.05, 250/559.06, 559.07, 559.08, 234, 235; 435/6.1, 6.11, 287.2; 382/129; 436/94, 436/800, 806; 348/345, 349–357

See application file for complete search history.

(56) References Cited

U.S. PATENT DOCUMENTS 6,885,454 B2 *  4/2005  Naya et al. .................... 356/445
7,217,573 B1    5/2007  Oshida et al.

(Continued)

FOREIGN PATENT DOCUMENTS

JP    2001-108684 A    4/2001
JP    2001-242081 A    9/2001

(Continued)

OTHER PUBLICATIONS

Office Action in Chinese Application No. 200980110931.4 (Nov. 25, 2011).

(Continued)

*Primary Examiner* — Pascal M Bui Pho
(74) *Attorney, Agent, or Firm* — Fitzpatrick, Cella, Harper & Scinto

(57) ABSTRACT

A scanning imaging device has a spot light projecting section 101 that irradiates a first spot light for excitation and two second spot lights for focus detection onto a flow channel of a substrate 4 and an imaging section 102 for picking up an image of light emitted from a target of detection in the flow channel as it is excited by the first spot light. One of the second spot lights is reflected at the top surface of the flow channel and the other of the second spot lights is reflected at the bottom surface of the flow channel and a focus position adjustment mechanism for adjusting the focus position of each of the first and second spot lights in the depth direction of the flow channel such that the quantity of deviation of the focus positions of the first and second spot lights in the depth direction of the flow channel as determined by comparing the intensities of the one and the other of the second reflected lights reflected at the flow channel.

13 Claims, 11 Drawing Sheets

(56) References Cited

U.S. PATENT DOCUMENTS

| | | | |
|---|---|---|---|
| 7,504,647 B2 * | 3/2009 | Amar et al. | 250/559.3 |
| 2003/0197112 A1 * | 10/2003 | Atkinson et al. | 250/201.6 |
| 2005/0118640 A1 * | 6/2005 | Kureshy et al. | 435/7.1 |
| 2005/0121596 A1 * | 6/2005 | Kam et al. | 250/201.2 |
| 2006/0146910 A1 * | 7/2006 | Koochesfahani et al. | 374/161 |

FOREIGN PATENT DOCUMENTS

| | | |
|---|---|---|
| JP | 2003-529076 A | 9/2003 |
| JP | 2003-294633 A | 10/2003 |
| JP | 2004-233114 A | 8/2004 |
| JP | 3551860 B | 8/2004 |
| JP | 2005-091134 A | 4/2005 |
| JP | 2005-527827 A | 9/2005 |
| JP | 2006-322707 A | 11/2006 |
| JP | 2006-349501 A | 12/2006 |
| WO | 01/73417 A1 | 10/2001 |
| WO | 03/083459 A1 | 10/2003 |
| WO | 03/100389 A1 | 12/2003 |
| WO | 03/100474 A2 | 12/2003 |

OTHER PUBLICATIONS

Office Action in Korean Application No. 10-2010-7023856 (Jun. 19, 2012).

* cited by examiner

SCANNING IMAGING DEVICE FOR IMAGING TARGET ON A SUBSTRATE

TECHNICAL FIELD

The present invention relates to a scanning imaging device for imaging a target substrate for detection, while adjusting the focus relative to the substrate. More particularly, the present invention relates to a scanning imaging device for detecting light emitted from a target of detection by irradiating excitation light to the target of detection arranged in a flow channel of a substrate.

BACKGROUND ART

A micro TAS technique of forming a micro flow channel in a substrate, flowing specimen DNA and a reagent into it to give rise to a biochemical reaction has been and being used in various technical fields and the usefulness and the advantages thereof are well known.

A technique of using an intercalator type fluorescence label for detecting the quantity of double-stranded DNA in a micro flow channel is also known. With this technique, double-stranded DNA is heated to about 50° C. to 90° C. and the temperature at which the double-stranded DNA dissociates into single-stranded DNA is determined to know the type of DNA by seeing the change of the fluorescence intensity.

However, a micro flow channel is very small and a cross section thereof shows a side thereof that is as short as several μm to hundreds of several μm. When observing the fluorescence intensity in a micro flow channel, while varying the temperature of the flow channel, the substrate is warped due to temperature changes and the flow channel is displaced. The substrate is deformed and the flow channel is displaced to a large extent particularly when the substrate is made of a plastic material. Additionally, the influence of auto-fluorescence of the substrate material should preferably be avoided when detecting weak fluorescence from a fluorescence label in a flow channel. For this purpose, preferably, the imaging area of the imaging device is minimized so as to pick up only fluorescence from a fluorescence label without receiving any auto-fluorescence. This can be achieved by means of a technique of raising the NA of the imaging optical system to reduce the depth of focus, a technique of detecting light on the basis of the principle of confocal imaging or that of light sectioning to reduce the imaging depth or some other similar technique. However, when the imaging depth is reduced by means of these techniques, fluorescence cannot be detected accurately unless the flow channel is so aligned that the imaging depth is accurately located in the flow channel. Additionally, there can arise a problem that fluorescence cannot be observed accurately because of a shift of the flow channel plane partially from the scanning plane due to deformation of the substrate, a manufacturing error of the flow channel, a positioning error and so on.

It may be conceivable to provide the imaging device with an auto-focusing mechanism as a measure for solving these problems. Japanese Patent Application Laid-open No. 2001-242081 discloses an auto-focusing mechanism that operates on a real time basis. The device is mounted on a device for detecting the fluorescence label bound to the probe of a DNA chip so as to receive excitation light reflected from the surface of the DNA chip by means of a quadrant photodiode and it is determined if the focal position is in front of or behind the target by seeing the differences of the quantities of light received by the four elements of the quadrant photodiode. Then, the lens position is adjusted to constantly keep the chip surface in focus.

Japanese Patent No. 3551860 discloses a device having an imaging system formed by using one-dimensional sensors (multi-channel photomultiplier tubes) and provided with an AF (auto-focusing) mechanism. Japanese Patent Application Laid-open No. 2006-322707 discloses a method of detecting the upper and lower walls of a flow channel by means of a quadrant photodiode and scanning between them in a zigzag manner.

The device disclosed in Japanese Patent Application Laid-open No. 2001-242081 is a device of a double scanning system. More specifically, a spot of excitation light is formed on a target of detection and produced fluorescence is led into a light amount detection element such as a photomultiplier tube (PMT) so as to acquire information on the entire surface of the target of imaging, while shifting the relative position of the spot of light on the target of imaging. This system is disadvantageous when the target of imaging is driven two-dimensionally for scanning because the scanning operation is time consuming and the device is bulky. Additionally, it is unrealistic to move a flow channel substrate containing liquid in the inside because bubbles may appear and liquid may leak out. The above-cited patent document also discloses a method of driving an optical head that includes an objective lens to be used for projecting excitation light and converging fluorescence, relative to a fixed target of imaging. While this method can drive the optical head to scan more quickly by means of a small drive unit if compared with moving a target of imaging, the use of a drive unit is a prerequisite for it so that the device is inevitably large and it is not free from the problem that the imaging operation is time consuming. Furthermore, it requires the use of a sensor dedicated to AF (auto-focusing). Still additionally, the optical head to be operated for scanning is inevitably heavy and the scanning operation is time consuming because the voice coil motor for driving the objective lens in the direction of the optical axis needs to be driven with the objective lens at the time of scanning operation.

The device disclosed in Japanese Patent No. 3551860 has an imaging system and a focus detection optical system and is adapted to only adjust the focus relative to a single spot. The focus is fixed during a scanning operation. Therefore, the focus cannot be adjusted on a real time basis to accommodate the positional shift of the flow channel while scanning a line.

The scanning method disclosed in Japanese Patent Application Laid-open No. 2006-322707 is a method to be applied to a double scanning scanner. It is not efficient because the scanning operation using it is time consuming.

DISCLOSURE OF THE INVENTION

Therefore, an object of the present invention is to provide a device that is suitable for acquiring an image by scanning, while adjusting the focus. More specifically, the object of the present invention is to provide a scanning imaging device that can excellently pick up an image of a target of detection by a single scanning operation if the target of detection is a substrate having a flow channel that is deformed or inclined.

In order to achieve the above object, a scanning imaging device according to the present invention comprises:
   an irradiation unit for irradiating at least a spot light for focusing onto a target substrate for detection;
   an optical system having a sensor array for receiving light from a target of detection in the target substrate for detection and the spot light reflected from the target substrate for detection; and a scanning unit for driving the optical system to scan the target substrate for detection at least in a main scanning direction, wherein the spot light is irradiated onto a position different from the target of detection in the target substrate for detection, and wherein the spot light reflected from the target substrate for detection is received to read out a signal from which a focusing signal and a detection signal are acquired.

In another aspect of the present invention, there is provided a scanning imaging device, comprising:

a spot light projection system for irradiating a first spot light for excitation to be irradiated onto a target of detection arranged in a flow channel formed in a substrate and two second spot lights for focusing to be irradiated onto the flow channel respectively at different positions on the substrate and scanning the first and second spot lights at least along the flow channel;

an imaging system for imaging light emitted from the target of detection excited by the first spot light, first reflected light produced by one of the second spot lights as a result of reflection at a top surface of the flow channel, and second reflected light produced by the other of the second spot lights as a result of reflection at a bottom surface of the flow channel; and a focus position adjustment system for adjusting focus positions of the first spot light and the second spot lights in a depth direction of the flow channel, wherein the focus position adjustment system is adapted to operate in accordance with a direction and a quantity of deviation of the focus positions of the first spot light and the second spot lights in the depth direction of the flow channel as determined by comparing an intensity of the first reflected light and that of the second reflected light.

Thus, according to the present invention, a signal of light at a focus position and a focus detection signal can be acquired by means of a sensor array and hence an appropriate scanning image can be acquired.

Additionally, the present invention provides a scanning imaging device that can image a target of detection by a single scanning operation even if the target of detection is a deformed or inclined flow channel.

Further features of the present invention will become apparent from the following description of exemplary embodiments with reference to the attached drawings.

BEST MODE FOR CARRYING OUT THE INVENTION

Now, an embodiment of scanning imaging device according to the present invention will be described below. Major targets of detection of the device of this embodiment are the quantity of double-stranded DNA in a micro flow channel, the quantity of target DNA that is bound to the probe of a DNA chip. In other words, a major objective of the device of this embodiment is detection of the presence or absence of a target substance by way of utilization of a phenomenon where optical characteristics change according to the presence or absence of a biochemical reaction. Target substances that can be used for the device also include proteins, ligands and microorganisms. Methods that can be used for observing a phenomenon where optical characteristics change include a method of coupling a labeling substance such as a fluorescent substance, a chemiluminescent substance or a dye either to a target substance or a probe that specifically captures a target substance and detecting the presence or absence of a reaction between them.

[A] Device Configuration

Figure 1:
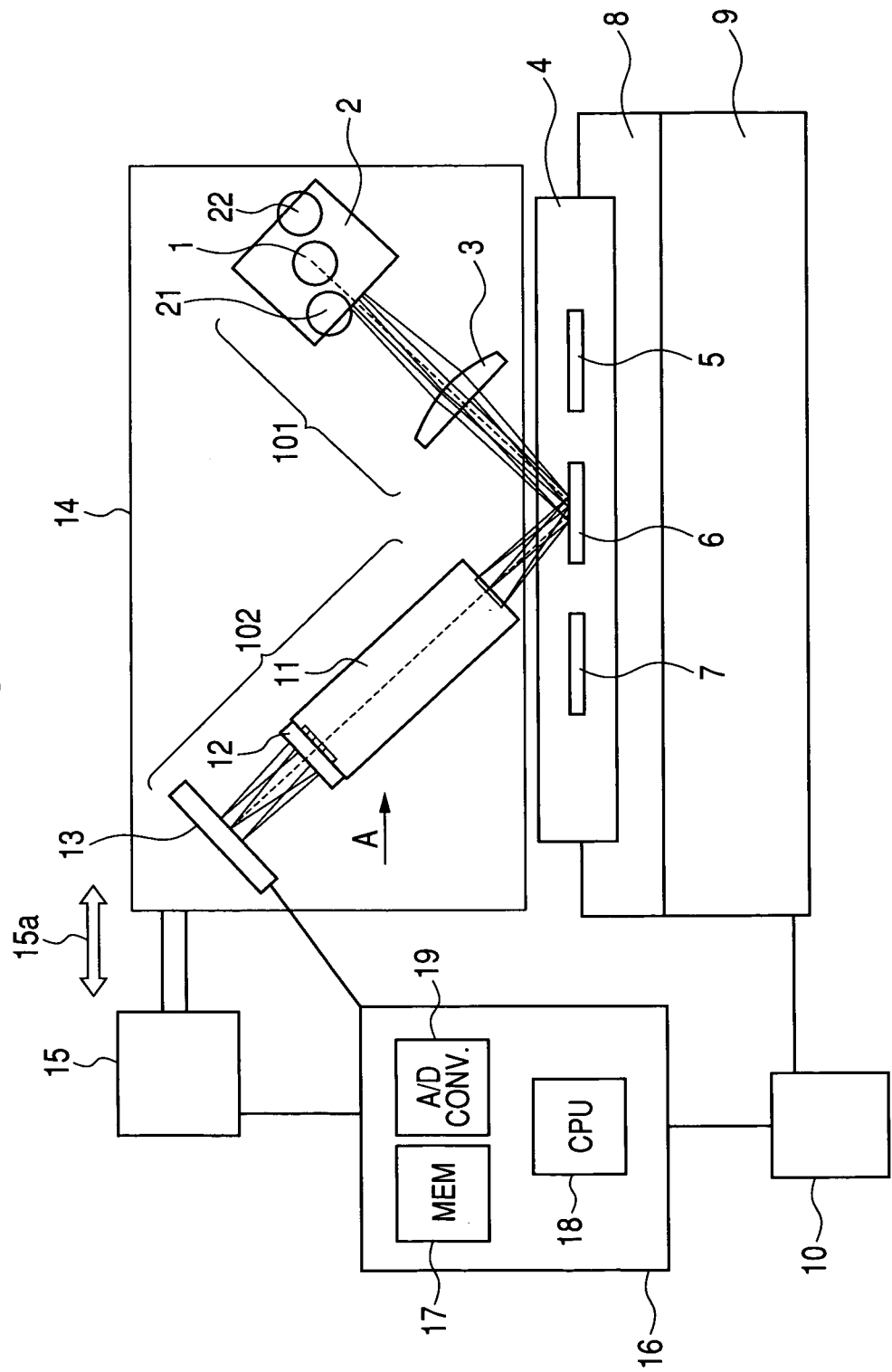
FIG. 1 is a schematic block diagram of an embodiment of scanning imaging device according the present invention, illustrating the configuration thereof.
Figure 2:
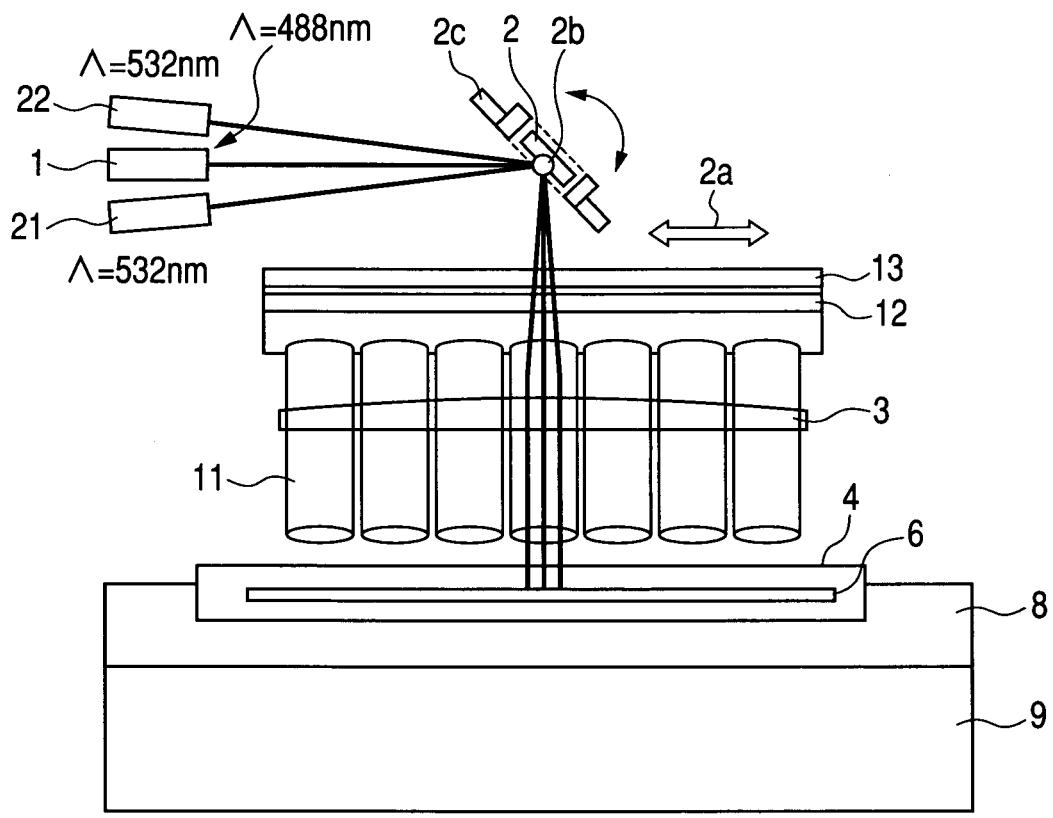
FIG. 2 is a schematic see-through view of a spot light projecting section, an imaging section, a substrate and so on illustrated in FIG. 1 as viewed in the direction of arrow A in FIG. 1.

FIG. 1 is a schematic block diagram of an embodiment of scanning imaging device according to the present invention, illustrating the configuration thereof. FIG. 2 is a schematic see-through view of a spot light projecting section, an imaging section, a substrate and so on illustrated in FIG. 1 as viewed in the direction of arrow A in FIG. 1.

The scanning imaging device of this embodiment includes a spot light projecting section 101 and an imaging section 102 arranged in a cabinet 14, a temperature adjusted block 8 supporting a substrate 4 where a plurality of micro flow channels 5, 6 and 7 are formed and a temperature adjusting section 9. The scanning imaging device of this embodiment further includes a drive section 15 for driving the cabinet 14 in the direction 15a illustrated in FIG. 1, a control circuit 16 having a memory 17, a CPU 18 and an A/D conversion section 19 and a temperature adjustment controlling section 10 for controlling the temperature of the temperature adjusting section 9.

The spot light projecting section 101 is an irradiation means for irradiating a spot light for focusing onto a target substrate for detection. The spot light projecting section 101 has a laser beam source 1 for emitting an excitation laser beam of a wavelength of 488 nm for exciting the fluorescence label added to the target of detection in the micro flow channels 5 through 7 and laser beam sources 21 and 22 for emitting focus detection laser beams of a wavelength of 532 nm. Therefore, the first spot light 1a (see FIG. 4) irradiated from the laser beam source 1 has the first wavelength (488 nm) while each of the two second spot lights 21a and 22a (see FIG. 4) irradiated respectively from the laser beam sources 21 and 22 has the second wavelength (532 nm). The spot light projecting section 101 further has a scanning section 2 formed by using a scanning mirror for scanning such laser beams and an fθ lens 3 for converting the scanning positions of the laser beams to positions proportional to the deflection angle of the scanning section 2. The spot light irradiated onto the substrate is converted into collimated light by the fθ lens 3.

Additionally, the imaging section 102 has a focusing element array (e.g., Selfoc lens array: tradename, available from Nippon Sheet Glass Co., Ltd.) 11 that is a focusing optical system, a fluorescence filter 12, and a line sensor 13 that is a sensor array. The fluorescence filter 12 has a property of blocking the light of the first wavelength (488 nm) for excitation while transmitting the fluorescence (wavelength of 500 nm to 530 nm) emitted from the fluorescence label that is excited by the first wavelength light and the light of the second wavelength (532 nm). Thus, an optical system having a sensor array for receiving the light from the target of detection in the flow channel of the target substrate for detection and the spot light reflected from the target substrate for detection is formed by these elements. With the above-described arrangement, the spot light irradiated for focusing and reflected by the flow channel can be received with the light from the target of detection by the sensor array. The reflected spot light for focusing can be separated from the fluorescence from the target of detection so that signals obtained by receiving the light coming from the target substrate for detection can be read out separately so as to acquire a focusing signal and a detection signal according to the signals.

The spot light for focusing is adapted to obtain information on positions different from the focus position. Preferably, two different spot lights are formed and an optical system is so arranged as to be able to acquire information on reflected light from the top surface and reflected light from the bottom surface of a flow channel. Then, the focus position can be defined to a position between the top surface and the bottom surface of the flow channel with ease in a manner as described below.

It should be noted here that only a single spot light may be formed if the focus position can be defined as a quantity of displacement from the reflected position of the spot light for focusing. If such is the case, the focus may, for example, be defined to a position not lower than 2 μm and not higher than 10 μm from the bottom surface of the flow channel.

The substrate 4 is provided with micro flow channels 5, 6 and 7 so as to correspond to different reagents of plural types, and target DNA of plural types and a fluorescence label as separated from each other by buffer solution are put in the micro flow channels 5, 6 and 7. The fluorescence label is of an intercalator type that is excited to emit fluorescence when it is taken into the two strands of double-stranded DNA (e.g., SYBR Green1: tradename, available from Molecular Probe). The excitation wavelength of such a fluorescence label is between 470 nm and 490 nm and adapted to emit fluorescence of a wavelength between 500 nm and 530 nm. The liquid is moved in the flow channel by a liquid transportation means (not illustrated). The substrate 4 is covered at the bottom surface thereof by a temperature adjusted block 8, which temperature adjusted block 8 is heated and cooled by the temperature adjusting section 9. Temperature of the temperature adjusting section 9 is controlled by the temperature adjustment controlling section 10.

The cabinet 14 containing the spot light projecting section 101 and the imaging section 102 is adapted to be driven to move, by a drive section 15 formed by using a stepping motor or a ultrasonic motor, in a sub-scanning direction 15a that is perpendicular to the main scanning direction 2a of the scanning section 2 (see FIG. 2). The scanning imaging device of this embodiment can pick up a fluorescence image of the fluorescence label in any of the flow channels 5 through 7 as it is driven to scan in the main scanning direction 2a of the scanning section 2 and move in the sub-scanning direction 15a of the cabinet 14 (i.e. the spot light projecting section 101 and the imaging section 102).

The focus detecting laser beams of the wavelength of 532 nm that are emitted from the respective laser beam sources 21 and 22 are transmitted through the fluorescence filter 12. The laser beams emitted from the light sources 21 and 22 are made to scan by the scanning section 2 like the laser beam emitted from the laser beam source 1. Reflected light of the laser beams from the top surface and reflected light of the laser beams from the bottom surface of any of the flow channels 5 through 7 are led to the line sensor 13 by the focusing element array 11.

The elements that form the focusing element array 11 are optical elements prepared by using a grated index type material. They produce an image of the target of imaging once in the inside of a set of lenses and then form an erected image of the target of imaging on an image plane. The focusing element array 11 is a member prepared by arranging such lenses on a straight line and can form an erected image of the target of imaging having a large area on the image plane.

The control circuit 16 that controls the entire scanning imaging device has a memory 17, a CPU 18 and an A/D conversion section 19 and operates for controlling the operation of the scanning section 2 and that of the line sensor 13. It also operates for controlling the temperature adjustment controlling section 10 and the drive section 15. The output from the line sensor 13 is transmitted to the A/D conversion section 19 under the control of the control circuit 16 and the outcome of the A/D conversion by the A/D conversion section 19 is sent to the memory 17.

The memory 17 has a memory region to be used for main scanning in a scanning operation in a region other than the region to be used by the control circuit 16 for controlling the device. The memory region for main scanning operates as a plurality of line memories for storing data of the line sensor 13. A partial region of the line memories is secured to store the data obtained by the line sensor 13 on all the pixels for the time period between the time when the spot light passes one of the pixels and the time when it passes the pixel for the next time. The above partial region of the line memories will be referred to as time slot data line memory hereinafter. Another region of the line memories is also secured for storing the values obtained from the data stored in the above partial region of the memories. The latter region of the line memories will be referred to as synthetic data line memory hereinafter.

Still other line memories are also secured as a region for storing the data of the synthetic data line memories corresponding to a plurality of times of main scanning in order to store two-dimensional data for the combination of main scanning and sub-scanning.

The scanning section 2 of the device of this embodiment may be formed by using a galvano-mirror, a MEMS mirror, a micro mirror array, a polygon mirror, etc. The focusing optical system of the device of this embodiment may be formed by using a focusing element array, a micro lens array or an ordinary focusing optical system. The sensor array of the device of this embodiment may be formed by using a line type CCD sensor, an area type CCD sensor having a plurality of lines, a line type CMOS sensor or an area type CMOS sensor having a plurality of lines.

[B] Detection

Now, the method of picking up an image of a fluorescence label in any of the flow channels 5 through 7 formed in the substrate 4 (fluorescence detection) by means of the above-described scanning imaging device will be described below by referring to FIGS. 1 and 2.

Note that any method other than the fluorescence detection method is the same in principle except that excitation light to be irradiated onto the focus position is not necessary.

The laser beam emitted from the laser beam source 1 is reflected by the scanning section 2 and converged to form a first spot light 1a having a diameter of about 10 μm by the fθ lens 3. The scanning section 2 is a micro mirror device that can freely rotate around two axes of rotation that are orthogonal relative to each other and include the reflection point of the laser beam. It operates for main scanning by angular oscillation that is centered at the first axis of rotation 2b and also for focus adjustment by angular adjustment that is centered at the second axis of rotation 2c. The laser beam that is reflected by the scanning section 2 oscillates reciprocally at a rate of about ten times per second in the main scanning direction 2a.

Figure 3:
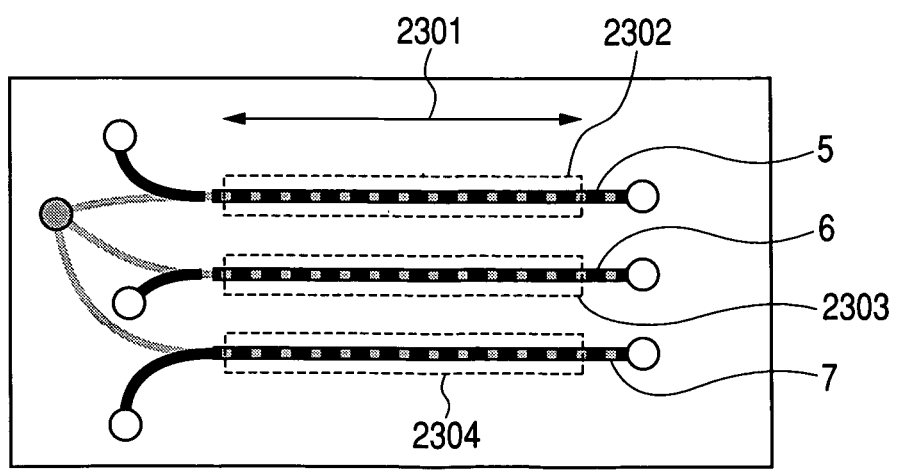
FIG. 3 is a schematic illustration of the main scanning direction of a spot light relative to a micro flow channel.

Then, as a result, the spot light is made to scan so as to make about ten round trips per second in a direction 2301 that is subsequently parallel to the flow channels 5, 6 and 7 as illustrated in FIG. 3. While the scanning is desirably constant speed scanning, it is difficult in reality to maintain the scanning speed to a constant level and the scanning gives rise to different speeds. Therefore, the scanning may be non-constant scanning showing a sinusoidal waveform. The reference position for starting the scanning of the spot light is detected when the spot light passes an optical sensor (not illustrated).

The beam reflection point of the scanning section 2 agrees with the focus position of the fθ lens 3. Therefore, the laser beam becomes a convergent light beam that is moved away by a distance proportional to the deflection angle produced by the scanning section 2 due to the refraction by the fθ lens 3 and proceeds in parallel with the optical axis. The focusing element array 11 and the line sensor 13 are arranged in such a way that the position of projection of the spot light and the light receiving section of the line sensor 13 are conjugated with each other. With this arrangement, only the region where the illumination light flux passes becomes an illuminated region so that the beam width becomes the imaging depth to make it possible to realize a highly accurate imaging (fluorescence detection) without an influence of auto-fluorescence. Therefore, when any of the flow channels 5 through 7 agree with the intersection of the imaging light path and the illumination light path, fluorescence emitted from the fluorescence label in the flow channel 5, 6 or 7, whichever appropriate, is led to the light receiving section of the line sensor 13 by the focusing element array 11.

As a scanning cycle of the scanning section 2 ends, the cabinet 14 containing the spot light projecting section 101 and the imaging section 102 is driven to move in the sub-scanning direction 15a that is perpendicular relative to the main scanning direction 2a by the drive section 15. In other words, the scanning section 2 operates for main scanning and the drive section 15 operates for sub-scanning. Thus, an image of the fluorescence in any of the imaging ranges 2302, 2303 and 2304 indicated by broken lines in FIG. 3 is picked up by the combination of main scanning and sub-scanning. The scanning operation can be conducted efficiently when main scanning is realized in a direction parallel to the longitudinal direction of the flow channels 5 through 7 as illustrated in FIG. 3 because sub-scanning can be made to skip the gaps separating the flow channels 5 through 7. Since small optical parts such as a focusing element array 11 are employed in this embodiment, such a skip can be made in short time.

[C] Focus Detection

Figure 4:
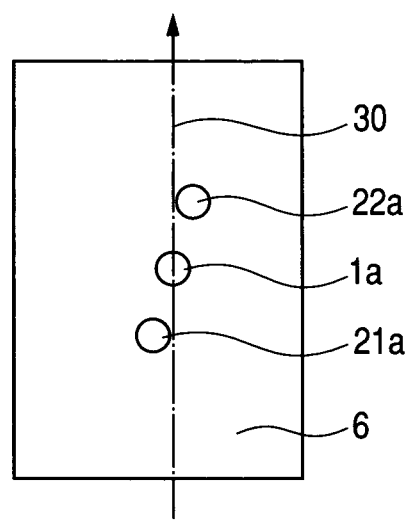
FIG. 4 is a schematic illustration of the positional relationship of spot lights emitted from respective laser beam sources in a micro flow channel.

As described above, the laser beam sources 21 and 22 are light sources respectively emitting laser beams of a wavelength of 532 nm. A beam of this wavelength is transmitted through the fluorescence filter 12. The laser beams emitted from the laser beam sources 21 and 22 are reflected by the scanning section 2 and converged to second spot lights 21a and 22a of a diameter of 10 μm by the fθ lens 3 like the above-described laser beam from the laser beam source 1. At this time, the laser beams are projected to positions that agree with the excitation spot light 1a on the reflection plane of the scanning section 2 but differ from the excitation spot light 1a on the plane where the flow channels 5 through 7 of the substrate 4 are formed as illustrated in FIG. 4. FIG. 4 is a schematic illustration of the positional relationship of spot lights 1a, 21a and 22a emitted from the respective laser beam sources 1, 21 and 22 in the micro flow channel 6. In FIG. 4, the arrow 30 of a broken line shows the locus of scanning of the spot light 1a and the spot lights 21a and 22a are displaced oppositely relative to each other in the scanning direction of the spot light 1a and in a direction perpendicular to that scanning direction and projected.

Figure 5:
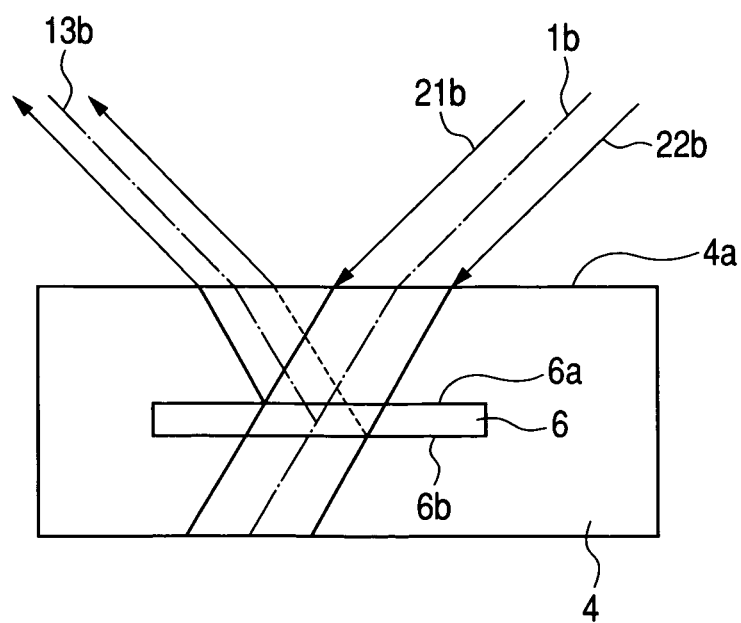
FIG. 5 is a schematic illustration of reflections of laser beams emitted from respective laser beam sources at the top surface and the bottom surface of a micro flow channel.

FIG. 5 schematically illustrates how the laser beams emitted respectively from the laser beam sources 1, 21 and 22 are reflected by the top surface and the bottom surface of a micro flow channel.

In the focused state where the intersection of the projection optical axis 1b of excitation light from the laser beam source 1 that is a source of excitation light and the imaging optical axis 13b of fluorescence that is emitted from the excited fluorescence label in the micro flow channel 6 is located in the micro flow channel 6, the optical axes 1b and 13b show a relationship as described below. That is, the projection optical axis 1b of excitation light from the laser beam source 1 and the imaging optical axis 13b of light entering the light receiving section of the line sensor 13 intersect each other at a position between the flow channel top surface 6a and the flow channel bottom surface 6b of the micro flow channel 6. In other words, the line sensor 13 receives only fluorescence emitted from the inside of the micro flow channel 6.

Excitation light excites the material of the substrate 4 all the way until getting to the flow channels 5 through 7 and after passing the flow channels 5 through 7 and the substrate 4 also emits auto-fluorescence. However, auto-fluorescence emitted at a position remote from the intersection with the imaging optical axis 13b is projected onto a position displaced in a direction perpendicular to the direction of arrangement of the pixels of the line sensor 13 as viewed from the pixels so that auto-fluorescence of the substrate 4 is never received by the line sensor 13 as a signal. Therefore, the line sensor 13 detects only fluorescence emitted from the inside of the micro flow channel 6 that is the object of detection of the line sensor 13. Thus, the line sensor 13 detects fluorescence with a good S/N ratio.

Figure 6:
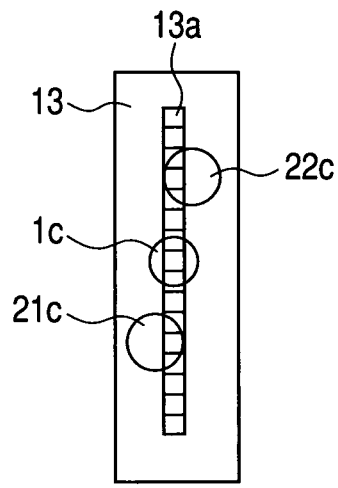
FIG. 6 is a schematic illustration of the positions of reflection images on a light receiving section of a line sensor.

Of the two spot lights 21a and 22a irradiated respectively from the laser beam sources 21 and 22, the spot light 21a irradiated from the laser beam source 21 is projected along the optical axis 21b onto an eccentric position relative to the projection optical axis 1b of excitation light on the top surface 4a of the substrate 4. Then, it proceeds toward the flow channel top surface 6a. Since the refractive index of the material of the substrate 4 and that of the fluid in the flow channel 6 differ from each other, the spot light 21a that is irradiated along the optical axis 21b is partly reflected at the flow channel top surface 6a. The first reflected light of the spot light 21a that is reflected by the flow channel top surface 6a is transmitted through the fluorescence filter 12 and led to the line sensor 13 by the focusing element array 11. As illustrated in FIG. 6, the reflection image 21c of the spot light 21a emitted from the laser beam source 21 that is formed on the flow channel top surface 6a is eccentric in a direction perpendicular to the direction of arrangement of the pixels of the light receiving section 13a of the line sensor 13 to such an extent that it partly lies on the line sensor 13.

Similarly, the other spot light 22a emitted from the laser beam source 22 also proceeds along the optical axis 22b as illustrated in FIG. 5 and projected to a position eccentric relative to the optical axis 1b at the side opposite to the optical axis 21b. The spot light 22a is partly reflected by the flow channel top surface 6a just like the spot light 21a that proceeds along the optical axis 21b, the remaining part of the spot light 22a is transmitted through the micro flow channel 6 and gets to the flow channel bottom surface 6b. Since the refractive index of the material of the substrate 4 and that of the fluid in the flow channel 6 differ from each other, the spot light 22a is also partly reflected at the flow channel bottom surface 6b. The second reflected light that is part of the spot light 22a reflected by the flow channel bottom surface 6b is transmitted through the fluorescence filter 12 and projected onto the line sensor 13 by the focusing element array 11. The reflection image 22c of the spot light 22a formed by the flow channel bottom surface 6b is led to a position eccentric relative to the light receiving section 13a at the side opposite to the reflection image 21c as illustrated in FIG. 6. At this time, the reflection image 22c is projected to a position that is eccentric relative to the light receiving section 13a of the line sensor 13 to such an extent that it partially lie thereon. Further, the reflection image 22c is projected to a position that is eccentric relative to the running direction of the line sensor 13 to such an extent that it does not lie on the reflection image 21c formed by the spot light 21a from the laser beam source 21 and the reflection image 1c of excitation light from the laser beam source 1.

The reflection image at the flow channel bottom surface 6b of the spot light 21a proceeding along the optical axis 21b and the reflection image at the flow channel top surface 6a of the spot light 22a proceeding along the optical axis 22b are projected to respective positions that are far away from the light receiving section 13a of the line sensor 13 than the reflection images 21c and 22c so that those reflection images are never recognized as signals by the line sensor 13.

Figure 7:
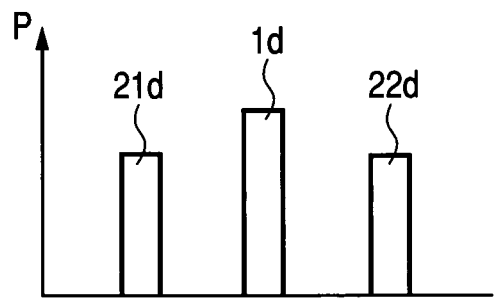
FIG. 7 is a graph illustrating the outputs from the pixels of the line sensor of FIG. 6 when the reflection images are received by the light receiving section of the line sensor illustrated in FIG. 6.

FIG. 7 is a graph illustrating the outputs P from the pixels of the line sensor of FIG. 6 when the reflection images 1c, 21c and 22c are received by the light receiving section 13a of the line sensor 13 illustrated in FIG. 6. In FIG. 7, reference symbols 1d, 21d and 22d respectively denote the outputs P of the reflection images 1c, 21c and 22c. As described above, when the projection optical axis 1b of excitation light and the imaging optical axis 13b intersect each other in the flow channel, the outputs P of the pixels of the light receiving region 13a of the line sensor 13 at the focus positions of the reflection images 21c and 22c are substantially equal to each other as indicated by reference symbols 21d and 22d in FIG. 7.

Figure 8:
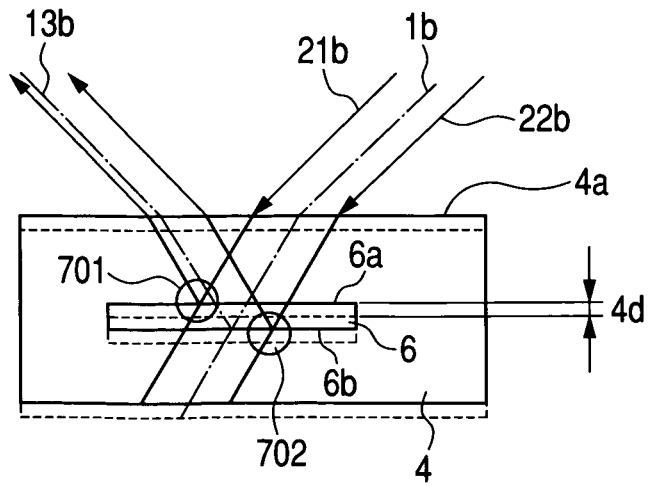
FIG. 8 is a schematic illustration of a state where the substrate and the micro flow channel formed in it are moved to a position located closer to a spot light projecting section and the imaging section by distance 4d from the position illustrated in FIG. 5.

FIG. 8 is a schematic illustration of a state where the substrate 4 and the micro flow channel 6 formed in it are moved to a position located closer to the spot light projecting section 101 and the imaging section 102 by distance 4d from the position illustrated in FIG. 5.

Figure 9:
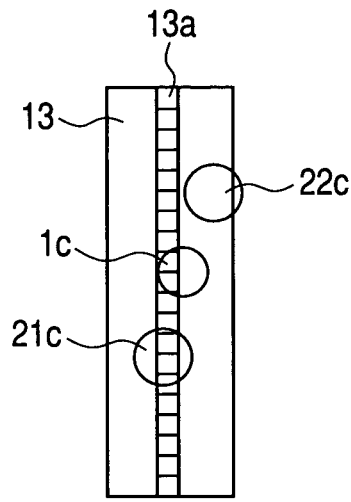
FIG. 9 is a schematic illustration of the positions of reflection images on the light receiving section of a line sensor in a state as illustrated in FIG. 8.
Figure 10:
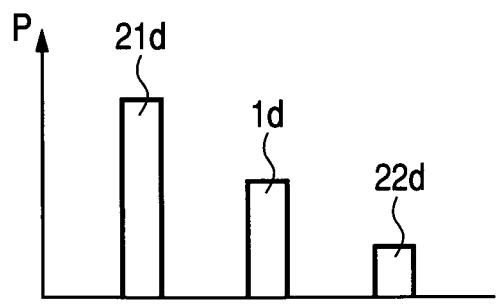
FIG. 10 is a graph illustrating the outputs from the pixels of the line sensor when the reflection images are received by the light-receiving section of the line sensor as illustrated in FIG. 9.

When the micro flow channel 6 shows a positional relationship as illustrated in FIG. 8 relative to the spot light projecting section 101 and the imaging section 102 (see FIG. 1), the light beam emitted from the laser beam source 21 and proceeds along the optical axis 21b is reflected at position 701 located close to the imaging optical axis 13b on the flow channel top surface 6a. The light beam that is emitted from the laser beam source 22 and proceeds along the optical axis 22b is reflected at position 702 located remote from the imaging optical axis 13b on the flow channel bottom surface 6b. Then, as a result, the reflection images 21c and 22c formed by the light beams that proceed respectively along these optical axes 21b and 22b show positional relationships relative to the light receiving section 13a of the line sensor 13 as illustrated in FIG. 9. In other words, while the reflection image 21c formed by the light beam coming from the laser beam source 21 is focused at a position close to the light receiving section 13a of the line sensor 13, the reflection image 22c formed by the light beam coming from the laser beam source 22 is focused at a position remote from the light receiving section 13a. In this way, when the micro flow channel 6 is located close to the spot light projecting section and the imaging section, the output 21d from the pixel of the light receiving section 13a of the line sensor 13 at the focus position of the reflection image 21c is stronger than the output 22d of the pixel at the focus position of the reflection image 22c (see FIG. 10).

Figure 11:
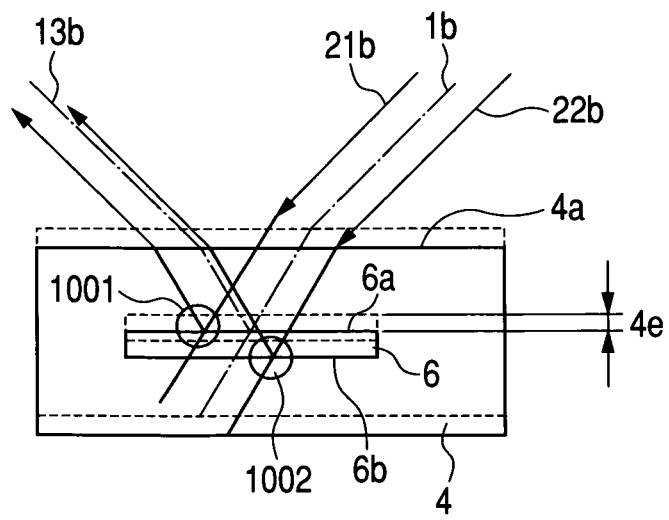
FIG. 11 is a schematic illustration of a state where the substrate and the micro flow channel formed in it are moved to a position located far away from the spot light projecting section and the imaging section by distance 4e from the position illustrated in FIG. 5.

FIG. 11 is a schematic illustration of a state where the substrate 4 and the micro flow channel 6 formed in it are moved to a position located far away from the spot light projecting section 101 and the imaging section 102 by the distance 4e from the position illustrated in FIG. 5.

Figure 12:
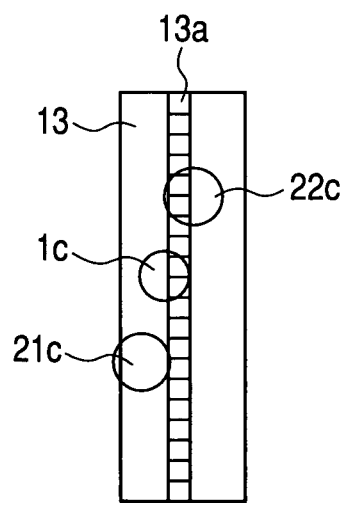
FIG. 12 is a schematic illustration of the positions of reflection images on the light receiving section of a line sensor in a state as illustrated in FIG. 11.
Figure 13:
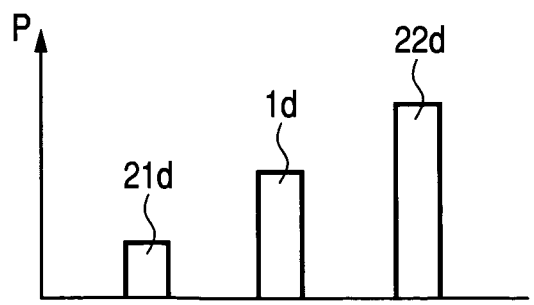
FIG. 13 is a graph illustrating the outputs from the pixels of the line sensor when the reflection images are received by the light-receiving section of the line sensor as illustrated in FIG. 12.

When the micro flow channel 6 shows a positional relationship as illustrated in FIG. 11 relative to the spot light projecting section 101 and the imaging section 102 (see FIG. 1), the light beam emitted from the laser beam source 21 and proceeds along the optical axis 21b is reflected at position 1001 located remote from the imaging optical axis 13b on the flow channel top surface 6a. The light beam that is emitted from the laser beam source 22 and proceeds along the optical axis 22b is reflected at position 1002 located close to the imaging optical axis 13b on the flow channel bottom surface 6b. Then, as a result, the reflection images 21c and 22c formed by the light beams that proceed respectively along these optical axes 21b and 22b show positional relationships relative to the light receiving section 13a of the line sensor 13 as illustrated in FIG. 12. In other words, while the reflection image 21c formed by the light beam coming from the laser beam source 21 is focused at a position remote from the light receiving section 13a of the line sensor 13, the reflection image 22c formed by the light beam coming from the laser beam source 22 is focused at a position close to the light receiving section 13a. In this way, when the micro flow channel 6 is located far away from the spot light projecting section and the imaging section, the output 21d from the pixel of the light receiving section 13a of the line sensor 13 at the focus position of the reflection image 21c is weaker than the output 22d of the pixel at the focus position of the reflection image 22c (see FIG. 13).

From the above, it will be seen that the distance between the spot light projecting section 101 and the imaging section 102 (see FIG. 1) and the micro flow channels 5 through 7 is so held that the intensities of the two reflection images 21c and 22c that are detected by the light receiving section 13a of the line sensor 13 are substantially equal to each other. In other words, when the above distance is held in that way, the intersection of the projection optical axis 1b of excitation light from the laser beam source 1 and the imaging optical axis 13b is located in one of the flow channels 5 through 7, the line sensor 13 can constantly catch fluorescence emitted from the fluorescence label in the corresponding one of the flow channels 5 through 7.

[D] Line Sensor Control

Figure 14:
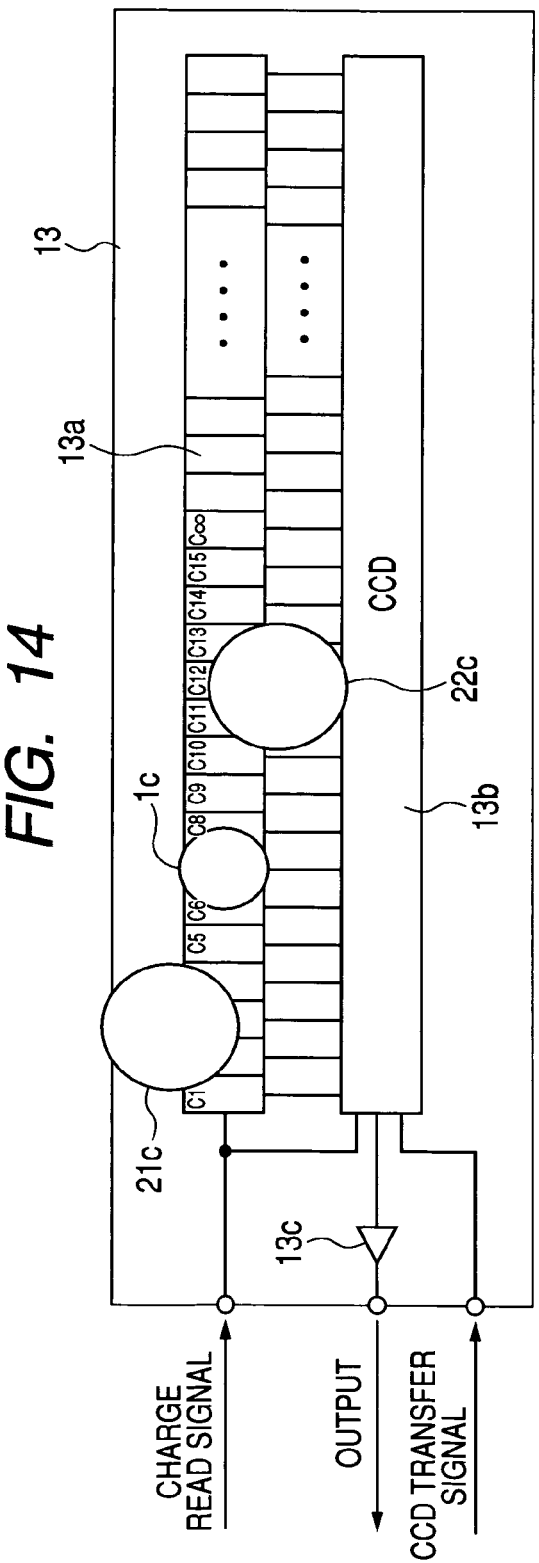
FIG. 14 is a schematic illustration of the configuration of the line sensor illustrated in FIG. 1.

FIG. 14 is a schematic illustration of the configuration of the line sensor illustrated in FIG. 1. As illustrated in FIG. 14, the light receiving section 13a of the line sensor 13 is formed by a plurality of pixels c1, c2, c3, . . . that are photoelectric conversion elements such as photodiodes and has a function of accumulating the electric charges produced as a result of photoelectric conversions. The line sensor 13 additionally has a CCD 13b for receiving the electric charges accumulated in the light receiving section 13a according to a charge read indication signal and an amplifier 13c for converting the accumulated electric charges of the pixels of the CCD 13b into voltage values sequentially in the order of arrangement of the pixels according to a CCD transfer indication signal. The CCD 13b receives the electric charges accumulated in the light receiving section 13a according to the charge read indication signal. Subsequently, the electric charges accumulated in the CCD 13b are sequentially output to the outside of the line sensor 13 by way of the amplifier 13c for converting the accumulated electric charges into voltage values sequentially in the order of arrangement of the pixels of the CCD 13b according to the CCD transfer indication signal.

FIG. 14 also illustrates how the reflection images 1c, 21c and 22c are virtually projected onto the pixels c1, c2, c3, . . . of the light receiving section 13a of the line sensor 13. The reflection images 1c, 21c and 22c move in the direction of arrangement of the pixels according to the scanning operation of the scanning section 2.

Now, the operation reading the signal from the line sensor 13 will be described below. While the reflection images 1c, 21c and 22c are sent to the light receiving section 13a by scanning, the control circuit 16 (see FIG. 1) repeats the operation of accumulating the electric charges of the pixels 13a of the line sensor 13 and that of reading the electric charges. For example, if the reflection images are scanned at a rate of 10 reciprocations per sec, the time spent for scanning a line is 50 msec. For sampling an image of a 20 mm long flow channel at a pitch of 10 μm, signals are read out from the line sensor 13 at sampling frequency=1/50 msec/10 μm*20 mm=40 kHz. Accumulation time at this time is 25 μsec.

Figure 15:
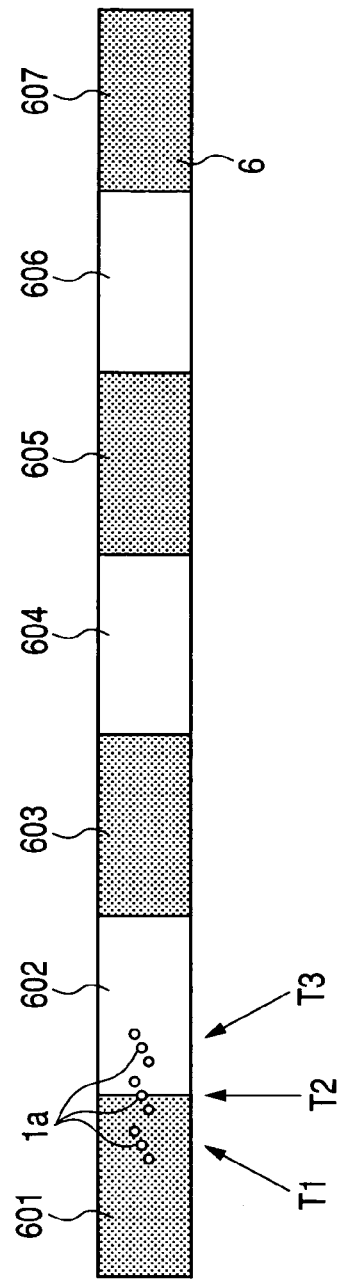
FIG. 15 is a schematic illustration of the positions of spot lights projected into a micro flow channel.

FIG. 15 is a schematic illustration of the positions of spot lights projected into the micro flow channel 6. A plurality of targets of detection 601, 603, 605 and 607 are arranged in the flow channel 6 with buffer solutions 602, 604 and 606 interposed among them. As time progresses from T1 to T2 and then to T3, the three spot lights move along the flow channel 6 in the rightward direction illustrated in FIG. 15 in response to the above-described scanning motion of the scanning section 2.

Figure 16A:
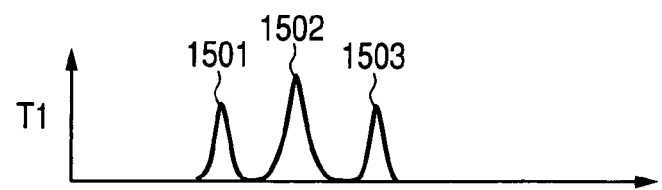
FIGS. 16A, 16B and 16C are graphs illustrating the waveforms of the signals read out from the line sensor when spot lights are projected into a micro flow channel as shown in FIG. 15.
Figure 16B:
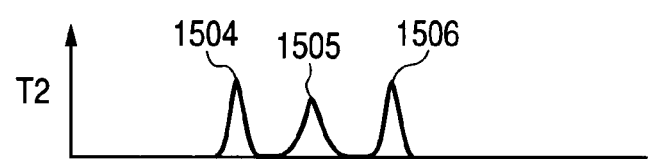
Figure 16C:
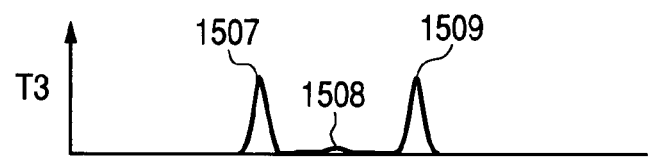

FIGS. 16A, 16B and 16C illustrate the waveforms of the signals read out at this time from the line sensor 13. In each of FIGS. 16A, 16B and 16C, the horizontal axis indicates the position in the direction of arrangement of pixels of the line sensor 13 and the vertical axis indicates the intensity of the signal from each pixel. The signal waveform at time T1 illustrated in FIG. 16A shows three peaks 1501, 1502 and 1503. Of the three peaks, the two peaks including the left peak 1501 and the right peak 1503 indicate the intensities of the reflection images 21c and 22c to be used for focus detection, whereas the central peak 1502 indicates the intensity of fluorescence coming from the inside of the flow channel 6 of the reflection image 1c formed by excitation light. A high intensity of fluorescence is obtained at time T1 because the excitation spot light 1a irradiates the target of detection 601. As indicated by the signal waveforms at time T2 in FIG. 16B, the detected intensity of fluorescence is weaker at time T2 than at time T1 because the excitation spot light 1a irradiates a spot between the target of detection 601 and the buffer solution 602 at time T2. Thus, the central peak 1505 at time T2 is lower than the central peak 1502 at time T1. Note, however, the intensities of the left and right peaks 1504 and 1506 at time T2 are not changed remarkably because they show the intensities of the reflection images from the flow channel top surface and the flow channel bottom surface respectively. As indicated by the signal waveforms at time T3 in FIG. 16C, the detected intensity of fluorescence (the height of the central peak 1508) is still weaker at time T3 than at time T2 because the excitation spot light 1a irradiates the buffer solution 602 at time T3.

Figure 17:
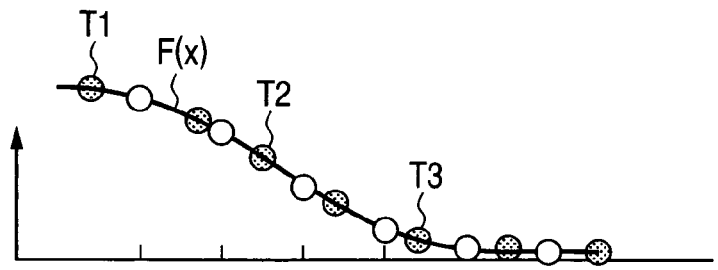
FIG. 17 is a graph illustrating the relationship between the positions (horizontal axis) of pixels arranged in a line sensor in the direction of arrangement thereof and the intensities of the signals (vertical axis) from the respective pixels.
Figure 18:
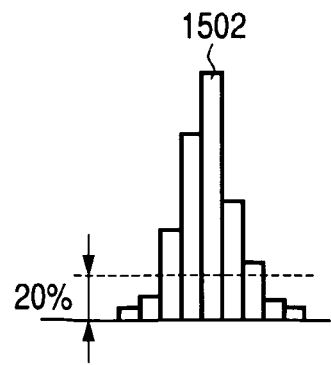
FIG. 18 is a graph showing the outputs from the respective pixels of a line sensor.

FIG. 17 is a graph showing the relationship between the positions (horizontal axis) of pixels arranged in the line sensor 13 in the direction of arrangement thereof and the intensities of the signals (vertical axis) from the respective pixels. The dark circles in FIG. 17 represent the values obtained from the actual waveforms showing the intensities of the signals. The positions of the dark circles correspond to the positions of the peaks 1502, 1505 and 1508 (FIGS. 16A, 16B and 16C)

showing the intensities of fluorescence. While the peaks are shown as those of curves in FIGS. 16A, 16B and 16C, they actually represent the peak outputs of the corresponding pixels of the line sensor as illustrated in FIG. 18. Thus, the position of each of the peaks may be determined by using a threshold value that is about 20% of the peak of intensity of fluorescence and finding the center of gravity or the center of area of the waveform. The height of each of the dark circles represents the value obtained by adding the outputs of the pixels that constitute the waveform of the peak 1502. Then, the coordinates of the dark circles that are determined in this way are plotted to obtain T1, T2 and T3 in FIG. 17. The other dark circles in FIG. 17 are also obtained from the actual waveforms. In this way, the electric charges of all the pixels of the line sensor 13 are read at a rate of 4 MHz. Thus, 2,000 sets of data, each set showing a waveform as illustrated in any of FIGS. 16A, 16B and 16C, are obtained by a single main scanning operation.

As pointed out above, it is difficult to maintain the scanning speed of the scanning section 2 to a constant level. In other words, the moving distance per unit time of a spot light varies according to the scanning speed. FIG. 17 illustrates an instance where the scanning speed gradually rises so that the intervals separating the dark circles in the horizontal direction gradually increases as the spot light proceeds. Since information that is obtained at constant distance intervals is required to form an image, intensity data of constant distance intervals as indicated by white circles in FIG. 17 need to be determined by computations. More specifically, the coordinate of each of the dark circles is defined as X and approximate polynomial $Y=F(X)$ for determining the intensity at X is defined. Then, X is sequentially substituted by the coordinates of points arranged at constant distant intervals to determine the intensities for those coordinates. An image formed by using the intensity data obtained in this way is positionally highly reliable and free from the influence of scanning speed errors and distortions. Additionally, all the obtained intensity data are based on a constant accumulation time and hence highly reliable.

The defocusing direction (whether the spot light projecting section and the imaging section are approaching or moving away from the flow channel) can be detected by detecting the intensities of two peaks of focus detecting spot lights as focusing signals and comparing them on a real time basis. Note that a constant intensity is obtained for the signals of two focus detecting spot lights regardless of the intensity of fluorescence produced by a spot light of excited light. Therefore, if the intensity of the central peak that represents the intensity of fluorescence produced by the spot light of excited light is low, the position of the central peak can be determined by using these signals. Since the position of the central peak is located between two focus detecting spot lights, it can be determined from the positions of the two focus detecting spot lights. Thus, an accurate image can be picked up because the peak position of signal intensity and hence the focus position can be accurately determined from the intensity signals obtained by using two focus detecting spot lights in the above-described manner.

The above-described method reads signals from all the pixels of the line sensor 13 at regular time intervals and records them in a memory while scanning spot lights. Thus, components that show a high processing rate need to be used for the A/D conversion section 19 (see FIG. 1) and other components and a large capacity memory 17 (see FIG. 1) is required. However, if the A/D conversion section does not show a high processing rate, it may alternatively be so arranged that approximate positions of the spot lights are stored in a memory in advance in order to scan the spot lights with a memory having a small capacity so as to take out the signals of only the pixels located around them. Such an arrangement can also acquire image information like the above-described method.

Since the positions of the spot lights are determined only by means of the angle of the scanning section 2 (see FIG. 1, etc.), the signal reading rate may be lowered to reduce the amount of data to be processed by detecting the angle of the scanning section 2 and reading information only on the pixels corresponding to the positions of the spot lights.

Figure 19:
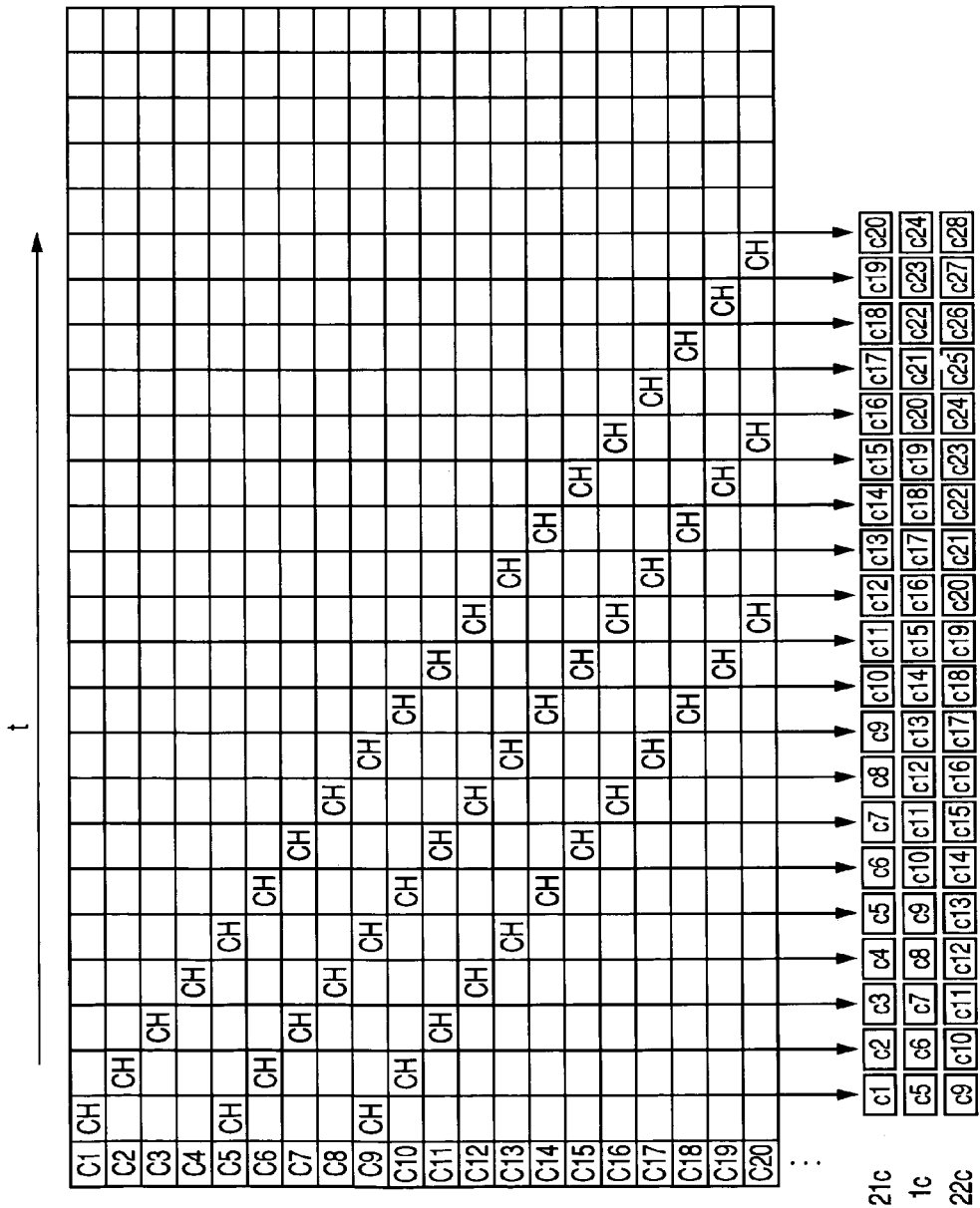
FIG. 19 is a schematic illustration of an accumulated state of electric charges of pixels and an operation of reading out the electric charges from the pixels of a line sensor.

FIG. 19 is a schematic illustration of an accumulated state of the electric charges of the pixels of the line sensor and an operation of reading out the electric charges from the pixels of the line sensor. In FIG. 19, pixels c1, c2, . . . , c20, . . . that are arranged sequentially in the line sensor are listed vertically, while the progress of time is horizontally indicated by t. The line sensor 13 of this embodiment is a CMOS sensor and the timing of reading the accumulated electric charge of each of the pixels thereof can be controlled externally. Thus, the main scanning angle of the scanning section 2 is detected and the electric charges of the charge accumulating pixels are sequentially read out in a switching manner in synchronism with the detected angle of the scanning section 2. Concretely, as shown by "CH"s in FIG. 19, firstly, electric charges are accumulated respectively in the pixels c1, c5 and c9 that correspond to the positions of the spot lights. Then, the electric charges read out from those pixels are subjected to A/D conversion at the A/D conversion section 19 before they are stored in the memory 17. At the same time, an operation of accumulating electric charges respectively in the next pixels c2, c6 and c10 is started. Then, the electric charges are read out and subjected to A/D conversion at the A/D conversion section 19 before they are stored in the memory 17. In this way, the intensities of the focus detecting spot lights 21c and 22c are detected in the above-described manner. The CPU 18 detects the defocusing direction and makes necessary corrections by sequentially reading out data from the memory 17 and comparing the intensities of the two spot lights 21c and 22c. Since the durations of accumulation of electric charges varies as pointed out earlier, preferably the durations are detected so as to correct the intensity of fluorescence of the spot light 1c.

As described above, the control circuit 16 compares the intensities of the first and second reflected lights (reflection images 21c and 22c) and determines the direction and the quantity of deviation of each of the spot lights 1a, 21a and 22a in the depth direction of the micro flow channel. Then, as will be described hereinafter, the focus position adjustment system is operated in response to the direction and the quantity of deviation to adjust the focus position of each of the spot lights 1a, 21a and 22a.

[E] Focus Correction

The focus position of each of the spot lights that are irradiated from the spot light projecting section 101 relative to any of the micro flow channels 5 through 7 in the substrate 4 can be adjusted by means of a focus position adjustment mechanism, which will be described below.

Firstly, a vertical drive mechanism (not shown) for driving the spot light projecting section 101 and the imaging section 102, which are arranged in the cabinet 14 as illustrated in FIG. 1, may be provided so as to move them in a direction perpendicular to the substrate 4 (in the depth direction of the micro flow channel). Then, the focus can be corrected by driving the spot light projecting section 101 and the imaging section 102 to move vertically so as to make the intensities of the two focus detecting reflection images 21c and 22c equal to each other. Note, however, that the spot light projecting section 101 and the imaging section 102 illustrated in FIG. 1 can be considerably heavy. Then, a large vertical drive mechanism may be required to drive them to move quickly.

The focus can also be corrected by driving only the spot light projecting section 101 to move vertically or horizontally relative to the substrate 4 by means of a vertical drive mechanism (not illustrated) or the drive section 15. With this arrangement, the load of the drive mechanism can be reduced to make it possible to correct the focus quickly because it is only necessary to drive the spot light projecting section 101 to move.

Secondly, means for scanning a spot light in the main scanning direction that is running along the longitudinal direction of the flow channels 5 through 7 of the substrate 4 and, at the same time, deflecting the spot light in the depth direction of the substrate 4 may be provided. The operation of focus correction can be conducted quickly without driving a large vertical drive mechanism when such a means is employed.

Figure 20:
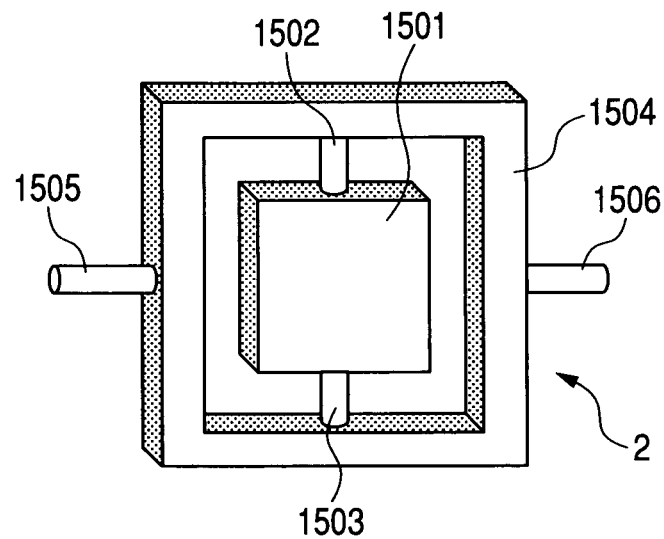
FIG. 20 is a schematic perspective view of a scanning section that can deflect a spot light in a main scanning direction and in the thickness direction of a substrate.

FIG. 20 is a schematic perspective view of a scanning section that can deflect a spot light in the main scanning direction (the first direction) that is running along the longitudinal direction of the flow channels and also in the second direction that is perpendicular to the first direction on a plane running in parallel with the top surface and the bottom surface of the flow channels. The scanning section 2 illustrated in FIG. 20 has a mirror section 1501 that is rotatably supported by a frame member 1504 by means of first shafts 1502 and 1503. Additionally, the frame member 1504 is rotatably supported by another frame member (not illustrated in FIG. 20) by means of second rotary shafts 1505 and 1506 that are orthogonal relative to the first shafts 1502 and 1503. The mirror section 1501 is driven under control to swing in the sense of rotation around the first shafts 1502 and 1503 by known driven means so as to operate a spot light for main scanning. The frame member 1504 that supports the mirror section 1501 is driven to rotate under control around the second shafts 1505 and 1506 by a known drive means so as to deflect the spot light in the depth direction of the substrate 4.

Figure 21:
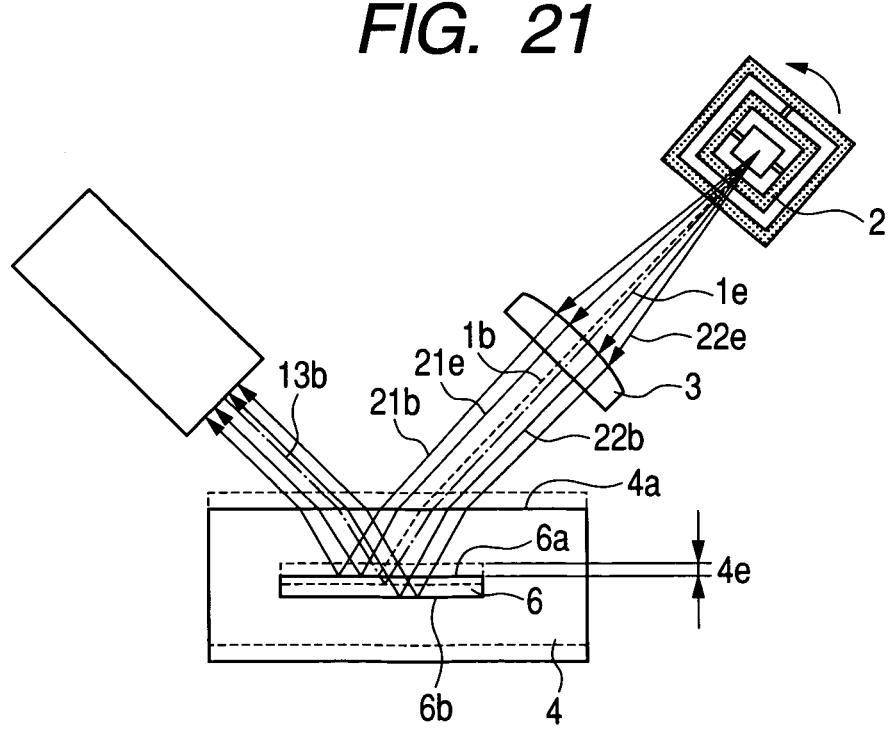
FIG. 21 is a schematic illustration of an operation of adjusting the focus of a spot light relative to a flow channel of a substrate by means of a scanning section as illustrated in FIG. 20.

Thus, when a defocused situation is detected in the vertical direction (depth direction) of the flow channels by focus detection signals (reflection images 21c and 22c) as described above, the scanning section 2 is angularly controlled and driven to turn to a direction inclined by 90° from the main scanning direction for focus control as illustrated in FIG. 21. For example, if the flow channel 6 is separated from the optical system by the distance 4e as illustrated in FIG. 11, the reflection image 21c is located at a position remote from the light receiving section 13a while the reflection image 22c is located at a position close to the light receiving section 13a as illustrated in FIG. 12 out of the spot lights that proceed along the optical axes 21b and 22b. Then, the light beams emitted from the light beam sources 21 and 22 are deflected downwardly as indicated by reference symbols 21e and 22e by rotating the scanning section 2 in a direction perpendicular to the main scanning direction for adjustment as illustrated in FIG. 21. Thus, as a result, the two reflection images of the light beams 21e and 22e can be formed at equidistant positions relative to the light receiving section 13a of the line sensor 13. Under this condition, the light beam that proceeds along the optical axis 1e formed by the light beam emitted from the excitation light source 1 intersects the imaging optical axis 13b at an intermediate position between the flow channel top surface 6a and the flow channel bottom surface 6b so that the line sensor 13 can efficiently catch the fluorescence image from the flow channel 6.

As the focus correction control operation is conducted on a real time basis while scanning laser spot lights, a fluorescence image of the fluorescence label in any of the flow channels can be efficiently picked up even if the flow channels 5 through 7 are displaced from the imaging plane formed by the imaging depth due to deformation or a manufacturing error on the part of the flow channels 5 through 7.

Only the position of projection of excitation light is shifted for focus correction in the above-described example so that there may arise an apprehension that the fluorescence detecting plane is shifted from the focal plane of the imaging element array 11 and the reflection images are not properly formed on the line sensor 13. However, the depth of focus of such a focusing element array is generally 200 to 300 μm and the observed value of a reflection image is not affected by a displacement of tens of several μm.

[F] Temperature Measurement

Now a method of measuring the temperature of the liquid in a flow channel while picking up a fluorescence image at the same time by means of a scanning imaging device as described above will be discussed below.

As pointed out above, techniques of heating or cooling a target of detection in a flow channel and examining the target on the basis of the information acquired on the change in the intensity of fluorescence at the same time are popular. It is important for such techniques to grasp the temperature of the target of detection over the entire imaging region. It is particularly important to accurately detect the temperature of the target of detection along with the intensity of fluorescence but no scanner that can measure the temperature of the target of detection and also detect fluorescence has been proposed to date.

A technique of measuring the temperature of the surface of the substrate to estimate the temperature in the flow channel may be conceivable. However, the temperature of the surface of a substrate is apt to be influenced by the environment and hence cannot be measured accurately. In short, the accuracy of detecting the intensity of fluorescence can be improved if it is possible to measure the temperature in the flow channel that changes incessantly along with fluorescence.

The reflectance of the top surface and the bottom surface of a flow channel is determined by the refractive index of the material of the substrate and the refractive index of the fluid flowing in the inside of the flow channel. The refractive index of the fluid flowing in the inside of the flow channel varies as a function of temperature as illustrated FIG. 22. Therefore, the temperature of the liquid in the flow channel can be determined from the intensity of light reflected by the top surface and the bottom surface of the flow channel.

Figure 22:
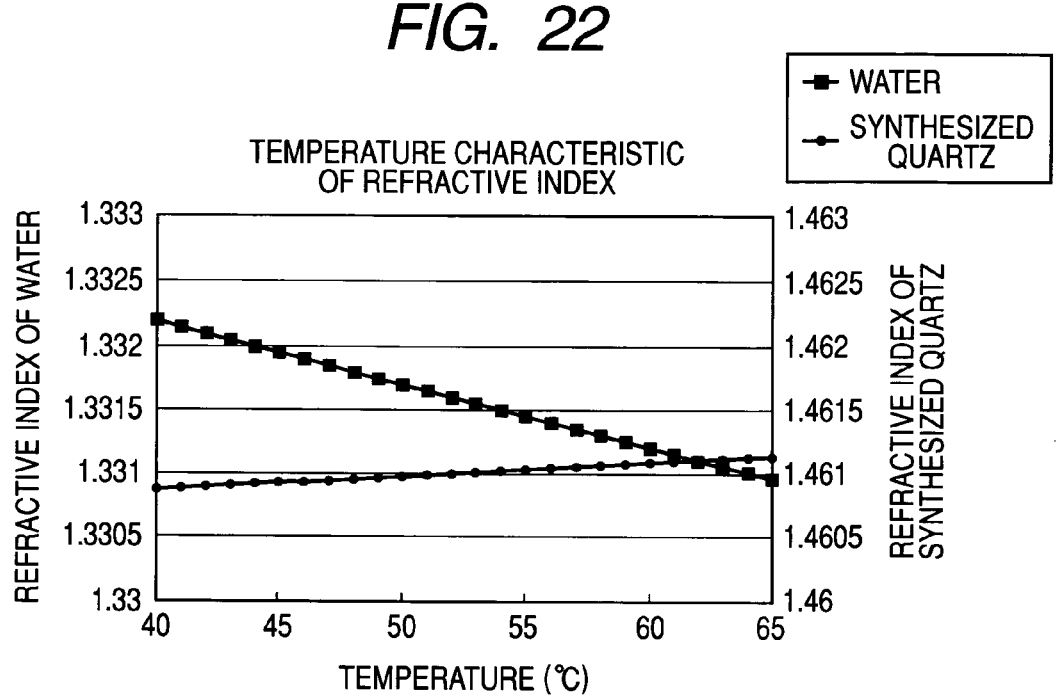
FIG. 22 is a graph illustrating the relationship between the refractive index of the material of a substrate and the refractive index of the fluid flowing in a flow channel of the substrate and the temperature of the substrate.

As illustrated in FIG. 22, the refractive index is 1.332 and 1.4609 respectively for water and quartz at 40° C., whereas it is 1.3317 and 1.4610 respectively for water and quartz at 50° C. and 1.3312 and 1.4611 respectively for water and quartz at 60° C. Therefore, if the angle of incidence of light entering a flow channel is 30° C., the reflectance is 0.403% at 40° C., 0.407% at 50° C. and 0.411% at 60° C. In other words, the rate of change of the intensity of reflected light relative to the temperature change is 0.407/0.403=1.01 when the temperature changes from 40° C. to 50° C. and 0.411/0.407=1.01 when the temperature changes from 50° C. to 60° C. In short, the intensity of reflected light changes by about 1% when the temperature changes by 10° C. The memory 17 of the control circuit 16 stores the correlations of the temperature of the substrate 4 and that of the liquid flown in the flow channel thereof and the reflectance of light at the interfaces of the flow channel (the flow channel top surface 6a and the flow channel bottom surface 6b) and the liquid at the temperatures.

Figure 23:
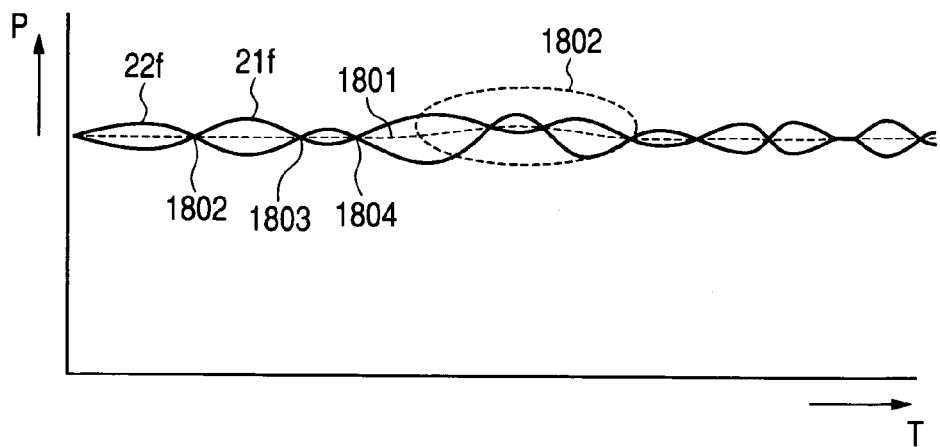
FIG. 23 is a graph illustrating the relationship of the intensities P of two reflection images in a single main scanning operation as indicated by the vertical axis and the time T as indicated by the horizontal axis of the graph.

FIG. 23 is a graph where the horizontal axis indicates time T and the vertical axis indicates the intensities P of the reflection images 21c and 22c during a main scanning cycle. The reference symbols 21f and 22f denote the intensities of the respective reflection images that are formed as the laser beams emitted from the focus detecting laser beam sources 21 and 22 are reflected at the top surface and the bottom surface of the flow channel, while the broken line 1801 shows the average values thereof. While the intensities 21f and 22f may fluctuate individually due to defocusing, they are constantly equal if the positions of the reflection images 21c and 22c are shifted as long as the temperature is constant. However, the average intensity 1801 changes as the temperature of the liquid in the flow channel changes and the reflectance changes due to the changes in the refractive indexes as described above. The average intensity is high in the region indicated by reference symbol 1802 in FIG. 23. This indicates that the reflectance is raised and hence the difference of refractive index between the substrate and the liquid is increased in and near the region. Then, it is seen that the refractive index of the liquid is made to fall and hence the temperature of the liquid is raised. The graph of the average intensities 1801 can also be obtained by smoothly linking the points where the two intensities 22f and 21f are equal to each other such as the points indicated by reference symbols 1802, 1803, 1804 and so on.

The CPU 18 of the control circuit 16 determines the reflectance of light at the flow channel top surface and the flow channel bottom surface from the ratio of the average intensity 1801 relative to the intensities of the laser beams (the second spot lights) emitted from the focus detecting laser beam sources 21 and 22. Note that information on the intensities of the laser beams emitted from the laser beam sources 21 and 22 is input to the control circuit 16. Then, the CPU 18 of the control circuit 16 can determine the temperature of the liquid in the flow channel from the correlation of the reflectance and the liquid temperature stored in the memory 17, using the obtained reflectance. The CPU 18 of the control circuit 16 can store the tendency of shift of the average value of the intensities of the two reflected light beams due to defocusing in advance and computationally determine the temperature of the liquid on the basis of the obtained values and the tendency.

Thus, with the above-described method, it is possible to detect the temperature of the liquid at the time when scanning fluorescence to detect the target of detection in the flow channel. Then, it is no longer necessary to provide the device with a special arrangement for detecting the temperature of the liquid in the flow channel so that the target of detection can be examined accurately without using a large device.

[G] Others

While the use of a line sensor as light detection means that is selected out of sensor arrays is described above, the light detecting (imaging) operation can alternatively be conducted by using an area sensor formed by two-dimensionally arranging image pickup elements. An area sensor is formed by arranging a plurality of line sensors and the above-described light detecting operation can be conducted by means of an area sensor and detecting light, using a particular line of the area sensor.

The scanning imaging device has a control circuit 16 including a memory 17, a CPU 18 and an A/D conversion section 19 as a control means and the control circuit 16 is connected to the scanning imaging device in the above description. However, the control circuit 16 may be replaced by an external computer (not illustrated) that operate as the memory 17, the CPU 18 and the A/D conversion section 19 and the computer may be connected to the scanning imaging device. Then, the external computer operates as a control means with such an arrangement.

While a fluorescence label is added to the target of detection as light emitting label and fluorescence emitted from the fluorescence label is detected in the above description. However, a label that can be used as light emitting label is by no means limited to such a fluorescence label. For example, a label adapted to emit phosphorescence may alternatively be added to the target of detection so as to detect phosphorescence emitted from the light emitting label.

The present invention is not limited to the above embodiments and various changes and modifications can be made within the spirit and scope of the present invention. Therefore, to apprise the public of the scope of the present invention, the following claims are made.

This application claims the benefit of Japanese Patent Application No. 2008-096145, filed Apr. 2, 2008, which is hereby incorporated by reference in its entirety.

The invention claimed is:

1. A scanning imaging device, comprising:
a first irradiation unit that irradiates a first spot light as a collimated light beam onto a target substrate for detection;
a second irradiation unit that irradiates a second spot light as a collimated light beam onto the target substrate for detection;
an optical system having a sensor array for receiving light from a target of detection existing at a focal position on a first plane in the target substrate for detection and the first spot light reflected at a second plane in the target substrate for detection and the second spot light reflected at a third plane in the target substrate for detection, the second and third planes being parallel to the first plane and displaced from the first plane in a thickness direction of the target substrate for detection; and
a scanning unit for driving the optical system to scan the target substrate for detection at least in a main scanning direction, which is parallel to the first plane,
wherein the first and second spot lights are irradiated onto respective positions each different from the focal position in the target substrate for detection,
wherein the first and second spot lights reflected from the respective positions in the target substrate for detection are received to read out a signal from which a focusing signal is acquired, and
wherein the first and second irradiation units are adapted for irradiating the first and second spot lights obliquely relative to the first plane.

2. The device according to claim 1, wherein the sensor array is a line sensor formed by arranging image pickup elements on a line so as to be capable of operating for addressing readout, and
wherein the device further comprises a control unit for reading out and storing outputs from the image pickup elements, the positions of which correspond to the spots.

3. The device according to claim 1, wherein the second plane is a set of upper and lower surfaces of a flow channel, and the upper and lower surfaces are located at different levels from the first plane in the target substrate for detection.

4. A scanning imaging device, comprising:
an irradiation unit that irradiates at least a spot light as a collimated light beam onto a target substrate for detection;
an optical system having a sensor array for receiving light detection existing at a focal position on a first plane in the target substrate for detection and the spot light reflected at a second plane from the target substrate for detection, the second plane being parallel to the first plane and displaced from the first plane in a thickness direction of the target substrate for detection; and a scanning unit for driving the optical system to scan the target substrate for detection at least in a main scanning direction, which is parallel to the first plane, wherein the spot light is irradiated onto a position different from the focal position in the target substrate for detection, wherein the spot light reflected from the target substrate for detection is received to read out a signal from which a focusing signal is acquired, wherein the irradiation unit is adapted for irradiating the spot light obliquely relative to the first plane, wherein the irradiation unit is adapted to irradiate two focusing spot lights and an exciting spot light to respective positions on the target substrate for detection that are different from each other, and wherein the scanning unit is a mirror that is adapted to deflect light in two directions under control for main scanning in parallel with the sensor array of the spot lights and for focus adjustment by deflection in a direction perpendicular to main scanning.

5. A scanning imaging device, comprising:

a spot light projection system for leading light beams from a light source for emitting a light beam of a first wavelength and a light source for emitting a light beam of a second wavelength to a target of imaging and forming at least two spot lights at different positions on the target of imaging to be scanned by a scanning unit;

an imaging optical system for forming respective images of the spot lights on a sensor array arranged in parallel with the scanning direction via a fluorescence filter adapted to block the light beam of the first wavelength and transmit the light beam of the second wavelength; and an arithmetic unit for computationally determining a temperature of liquid in a flow channel based on an intensity of the image formed by the light beam of the second wavelength.

6. A scanning imaging device comprising:

a spot light projection system for irradiating a first spot light for excitation onto a target of detection arranged at a focus position in a flow channel having a top surface and a bottom surface formed in a substrate, the top surface being parallel to the bottom surface and displaced from the bottom surface in a thickness direction of the substrate, and two second spot lights collimated for focusing onto the flow channel respectively at different positions in the substrate and scanning the first and second spot lights at least along the flow channel;

an imaging system for imaging light emitted from the target of detection excited by the first spot light, first reflected light produced by one of the second spot lights as a result of reflection at the top surface of the flow channel, and second reflected light produced by the other of the second spot lights as a result of reflection at the bottom surface of the flow channel; and a focus position adjustment system for adjusting the focus position of the first spot light in a depth direction of the flow channel, wherein the spot light projection system is adapted for irradiating the spot lights obliquely relative to the top and bottom surfaces of the flow channel, and wherein the focus position adjustment system is adapted to operate in accordance with a direction and a quantity of deviation of the focus position of the first spot light in the depth direction of the flow channel as determined by comparing an imaged intensity of the first reflected light and that of the second reflected light.

7. The device according to claim 6, wherein the spot light projection system has a scanning unit for deflecting the first and second spot lights in two directions including a first direction running along the flow channel and a second direction orthogonal to the first direction on a plane that is parallel to the top surface and the bottom surface of the flow channel, and wherein the focus positions are adjusted by deflection of the first and second spot lights in the second direction by means of the scanning unit.

8. The device according to claim 6, wherein the focus position adjustment system is constituted by a drive mechanism for driving the spot light projection system, or both the spot light projection system and the imaging system, in the depth direction of the flow channel.

9. The device according to claim 6, wherein the imaging system has a line sensor having a plurality of pixels arranged in a direction parallel to a running direction of the flow channel.

10. The device according to claim 6, wherein the first spot light has a first wavelength and the two second spot lights have wavelengths different from the first wavelength, and wherein the imaging system has a filter adapted to block the light beam of the first wavelength and transmit a light beam of a wavelength different from the first wavelength emitted from the target of detection and the light beam of the wavelengths of the two second spot lights.

11. The device according to claim 6, wherein the device is connected to a control unit that compares the intensity of the first reflected light and that of the second reflected light to determine the direction and the quantity of deviation of the focus positions of the first and second spot lights in the depth direction of the flow channel and adjusts the focus positions by operating the focus position adjustment system in accordance with to the direction and the quantity of deviation.

12. The device according to claim 11, wherein the control unit is adapted to determine a temperature of liquid in the flow channel based on an intensity of the first reflected light and that of the second reflected light.

13. A scanning imaging device comprising:

a spot light projection system for irradiating a first spot light for excitation to be irradiated onto a target of detection arranged in a flow channel formed in a substrate and two second spot lights for focusing to be irradiated onto the flow channel respectively at different positions on the substrate and scanning the first and second spot lights at least along the flow channel;

an imaging system for imaging light emitted from the target of detection excited by the first spot light, first reflected light produced by one of the second spot lights as a result of reflection at a top surface of the flow channel, and second reflected light produced by the other of the second spot lights as a result of reflection at a bottom surface of the flow channel; and a focus position adjustment system for adjusting focus positions of the first spot light and the second spot lights in a depth direction of the flow channel, wherein the focus position adjustment system is adapted to operate in accordance with a direction and a quantity of deviation of the focus positions of the first spot light and the second spot lights in the depth direction of the flow channel as determined by comparing an intensity of the first reflected light and that of the second reflected light, wherein the device is connected to a control unit that compares the intensity of the first reflected light and that of the second reflected light to determine the direction and the quantity of deviation of the focus positions of the first and second spot lights in the depth direction of the flow channel and adjusts the focus positions by operating the focus position adjustment system in accordance with to the direction and the quantity of deviation, wherein the control unit is adapted to determine a temperature of liquid in the flow channel based on an intensity of the first reflected light and that of the second reflected light, wherein the control unit stores a correlation of the temperature of liquid and a reflectance of light at the top surface and the bottom surface of the flow channel, and wherein the control unit determines the reflectance from a ratio of an average intensity of the first reflected light and the second reflected light imaged by the imaging system relative to an intensity of the second spot light irradiated from the spot light projection system and then determines the temperature of the liquid according to the correlation.

* * * * *